United States Patent [19]

Hamaoka et al.

[11] Patent Number: 4,672,106

[45] Date of Patent: Jun. 9, 1987

[54] MURAMYLPEPTIDE ACTIVE ESTER DERIVATIVES

[75] Inventors: Toshiyuki Hamaoka, Officer Residence No. 1022, 730 Gakuen Daiwa-cho 5-chome, Nara-shi, Nara; Hiromi Fujiwara, Hyogo; Tsuneo Kusama; Masahiro Komiya, both of Tokyo, all of Japan

[73] Assignees: Toshiyuki Hamaoka; Daiichi Seiyaku Co., Ltd., both of Japan

[21] Appl. No.: 770,471

[22] Filed: Aug. 29, 1985

[30] Foreign Application Priority Data

Aug. 29, 1984 [JP] Japan ................. 59-178209

[51] Int. Cl.$^4$ ............ A61K 37/00; A61K 37/02
[52] U.S. Cl. .................. 530/331; 536/53
[58] Field of Search ........... 536/53; 514/2, 8, 18, 514/19; 530/300, 331; 260/998.2

[56] References Cited

U.S. PATENT DOCUMENTS

| 4,369,178 | 1/1983 | Yamamura et al. | 514/8 |
| 4,406,889 | 9/1983 | Hartmann et al. | 514/8 |
| 4,548,923 | 10/1985 | Hartmann et al. | 514/8 |

Primary Examiner—John Kight
Assistant Examiner—Nathan M. Nutter
Attorney, Agent, or Firm—Sughrue, Mion, Zinn, Macpeak and Seas

[57] ABSTRACT

Muramylpeptide active ester derivatives represented by the formula:

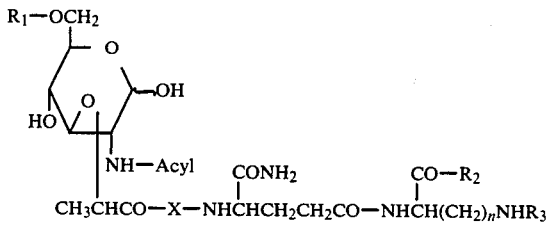

wherein $R_1$ represents a hydrogen atom or a fatty acid residue having from 2 to 10 carbon atoms; —$COR_2$ represents an active ester group; $R_3$ represents a fatty acid residue having from 1 to 10 carbon atoms; X represents an alanine, N-methylalanine or valine residue; "Acyl" represents a fatty acid residue having from 2 to 6 carbon atoms; and n represents an integer of from 1 to 6. These compounds are applicable as haptens for the immunotherapy and exhibit antitumor activity.

11 Claims, No Drawings

MURAMYLPEPTIDE ACTIVE ESTER DERIVATIVES

FIELD OF THE INVENTION

This invention relates to novel muramylpeptide active ester derivatives having excellent antitumor activity. More particularly, this invention relates to muramylpeptide active ester derivatives represented by the formula (I):

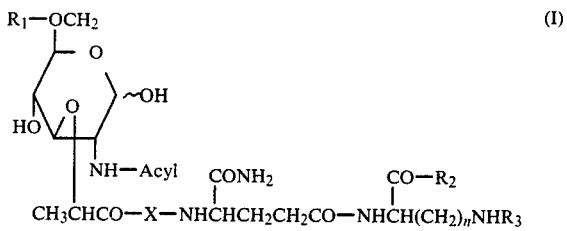

wherein $R_1$ represents a hydrogen atom or a fatty acid residue having from 2 to 10 carbon atoms; $-COR_2$ represents an active ester group; $R_3$ represents a fatty acid residue having from 1 to 10 carbon atoms; X represents an alanine, N-methylalanine or valine residue; "Acyl" represents a fatty acid residue having from 2 to 6 carbon atoms; and n represents an integer of from 1 to 6.

BACKGROUND OF THE INVENTION

With the recent development of study on enhancement of immune response aiming at antitumor effect, further detailed studies on immunological antitumor activities have been conducted.

Enhancement of immune response includes enhancements of humoral immunity, cell-medicated immunity, macrophage function, etc. With respect to cell-mediated immunity, an attempt to enhance effector T cells (hereinafter referred to as "$T_E$ cells") has been investigated.

$T_E$ cells receive a great deal of attention since they, when induced in a living organism, react specifically with tumor cells produced in the living organism to destroy the tumor cells.

The present inventors considered the mechanism of $T_E$ cells generation in a living organism as summarized in what follows.

In case normal cells are transformed into tumor cells, "tumor associated antigens" appear in the tumor cells. On the other hand, when tumor-bearing hosts are immunized with hapten-modified autologous cells, hapten-reactive helper T cells are induced. In this condition, if the tumor surface is modified with hapten, the preinduced hapten-reactive helper T cells can enhance generation of $T_E$ cells specific to the tumor cells. The $T_E$ cells recognize the tumor associated antigens and destroy the tumor cells.

The term "hapten" herein used means an incomplete antigen which per se lacks immunogenicity but, upon being conjugated to autologous serum proteins or autologous cell surfaces, potentially induces T cell activity in vivo.

The present inventors found 2,4,6-trinitrophenyl group (TNP) to be capable of playing a role as a hapten exhibiting immune response specific to tumor cells and proved the above-described reaction mechanism (*J. Exp. Med.*, 149, 185–199 (1979) and *J. Immunol.*, 124, 863–869 (1980)). However, application of the immunotherapy using TNP as hapten to tumors in human is not satisfactory in view of toxicity of TNP and the like.

SUMMARY OF THE INVENTION

The present inventors made various attempts to find a substance suitable as a hapten that is easily conjugated to surfaces of tumor cells by mixing therewith to potentiate tumor specific immunity, is of low toxicity and is clinically applicable. As a result, it has now been found that active ester derivatives of muramylpeptides represented by the above-described formula (I) satisfy the above requirements and the present inventors completed the invention.

In addition, it is hitherto known that tubercle bacillus (*Bacillus tuberculosis*) has potential immunogenicity to not only animals but humans from the fact that subcutaneous injection of tuberculin protein or tubercle bacillus-related substances to the person who has been inoculated with BCG vaccine induces tuberculin hypersensitivity.

Therefore, if the compound according to the present invention share antigenic determinants to BCG and cancer patient is a tuberculin-positive state spontaneously or BCG vaccination, the immunization of the cancer patient with the autologous tumor cells which are modified with the compound of this invention induces a strong tumor-specific immunity promptly. This possibility is of great clinical advantage.

Examinations based on the above-described viewpoint confirmed that the compound according to the present invention shares antigenic determinants to BCG and ensured the effectiveness of the compound of this invention.

Japanese Patent Application (OPI) No. 42398/84 (the term "OPI" as used herein refers to a "published unexamined Japanese patent application") describes that a muramyldipeptide active ester derivative has a tumor specific immunity. The present inventors found that muramyltripeptide active ester derivatives of this invention formed by introducing a basic α-amino acid to the muramyldipeptide active ester derivatives have more excellent tumor specific immunity, and completed the present invention.

DETAILED DESCRIPTION OF THE INVENTION

The above-described formula (I), the active ester group represented by $-COR_2$ characterizes the compounds of the present invention. In the formula $-COR_2$, $R_2$ includes a p-nitrophenoxy group, a 2,4-dinitrophenoxy group, a 2,4,5-trichlorophenoxy group, a pentachlorophenoxy group, a pentafluorophenoxy group, a phenylthio group, a succinimidooxy group, a benzotriazolyloxy group, a 5-norbornene-2,3-dicarboxyimidooxy group, a phthalimidooxy group, a morpholinooxy group, a piperidinooxy group, a 2-pyridylthio group, a 2-pyridyloxy group, a 3-pyridyloxy group, an 8-quinolyloxy group and a 2-hydroxyphenoxy group, etc.

The fatty acid residue represented by $R_1$, $R_3$ or "Acyl" means a group derived from the corresponding aliphatic carboxylic acid, and a hydroxyl group has been removed from the carboxyl group thereof. Specific examples of the fatty acid residue include a formyl group, an acetyl group, a propionyl group, a butyryl group, a valeryl group, a hexanoyl group, a heptanoyl group, an octanoyl group, a nonanoyl group, a decanoyl group, an isobutyryl group, an isovaleryl group, a pivaloyl group, an acryloyl group, a propioloyl group, a methacryloyl group, a crotonoyl group, an isocrotonoyl group and the like.

Of the compounds represented by the formula (I), a preferred class of compounds includes those having the formula (I) wherein n represents 4, $R_1$ represents a hydrogen atom, and $R_3$ represents a fatty acid residue having from 2 to 4 carbon atoms. More preferred compounds are those having the formula (I) wherein X represents an alanine residue or a valine residue, n represents 4, $R_1$ represents a hydrogen atom, Acyl and $R_3$ represent acetyl groups, and $R_2$ represents a 3-pyridyloxy group.

The compound of the formula (I) of the present invention can be prepared by reacting a compound represented by the formula (II):

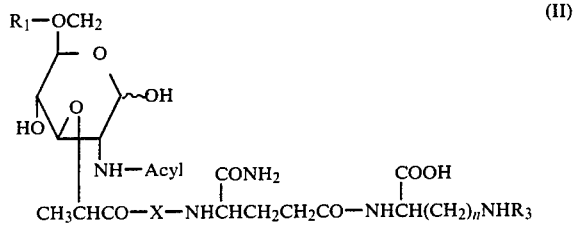

wherein $R_1$, $R_3$, X, Acyl and n are as defined above, with a compound represented by the formula (III):

$$R_2—H \quad (III)$$

wherein $R_2$ is as defined above, according to a condensation process generally employed for peptide synthesis, for example, a mixed acid anhydride process or a carbodiimide process, preferably a carbodiimide process.

According to a carbodiimide process, the condensation reaction can usually be carried out in the presence of dicyclohexylcarbodiimide in a solvent, such as tetrahydrofuran, chloroform, N,N-dimethylformamide, pyridine, etc., and a mixture thereof, at a temperature of from about 0° to about 80° C., preferably from about 20° to about 40° C., for a period of from about 1 hour to about 2 days. In this reaction, dicyclohexylcarbodiimide is used in an amount of from about 1 to about 2 mols, preferably from 1.0 to 1.2 mols, per mol of the compound (II), and the compound (III) is used in an amount of from about 1 to about 2 mols, preferably from 1.0 to 1.2 mols, per mol of the compound (II). After the reaction, the compound (I) can be isolated from the reaction mixture by a conventional method employed in peptide synthesis, such as extraction, solvent fractionation, reprecipitation, recrystallization, chromatography, etc.

The starting compound of the formula (II) which can be used in the preparation of the compounds of the present invention can be obtained by reacting a compound represented by the formula (IV):

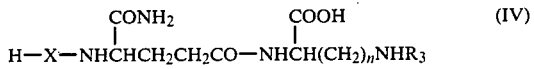

wherein $R_3$, X and n are as defined above, with an N-acylmuramic acid; or by condensating a compound represented by the formula (V):

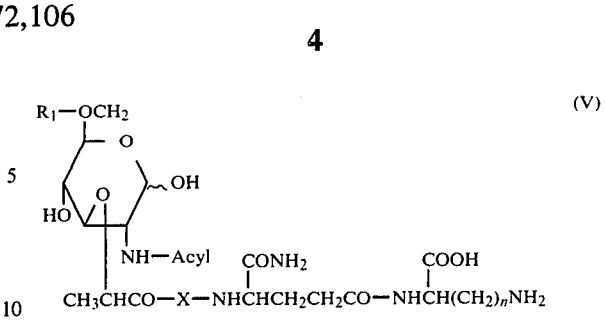

wherein $R_1$, Acyl, X and n are as defined above, with a compound represented by the formula (VI):

$$R_3—OH \quad (VI)$$

wherein $R_3$ is as defined above.

The compound of this invention has an excellent anti-tumor activity and is useful as a novel haptenic reagent in the manipulation of tumor specific immunity.

Regarding administrations of the compound of this invention, the compound of this invention is conjugated to attenuated tumor cells from a cancer patient and then the conjugate can be administered in a form of injections to the patient. Also, the compound of this invention can be administered in a form of intratumoral injections to a cancer patient when the patient bears a solid tumor.

The present invention will now be illustrated in greater detail with reference to Examples and Test Examples which are given for illustrative purposes only but not for limitation.

EXAMPLE 1

(1) In 40 ml of acetic acid was dissolved 4.00 g of $N^\alpha$-(t-butyloxycarbonyl-alanyl-D-isoglutaminyl)-$N^\epsilon$-benzyloxycarbonyl-lysine benzyl ester, and the solution was hydrogenolyzed in the presence of palladium-on-carbon in a hydrogen stream at room temperature. The catalyst was removed by filtration, and the filtrate was concentrated. To the residue was added diethyl ether, and the precipitated powder was recrystallized from methanoldiethyl ether to obtain 2.37 g of $N^\alpha$-(t-butyloxycarbonylalanyl-D-isoglutaminyl)-lysine.

(2) In 12 ml of N,N-dimethylformamide was suspended 1.50 g of the above obtained compound, and 0.89 g of N-hydroxy-5-norbornene-2,3-dicarboxyimide active ester of acetic acid and 0.40 ml of N-methylmorpholine were added to the suspension with stirring under ice-cooling. After 30 minues, the reaction mixture was allowed to warm to room temperature, followed by allowing the mixture to react overnight. The reaction mixture was concentrated, and diethyl ether was added to the residue. The precipitated powder was collected by filtration and recrystallized from methanol-diethyl ether to obtain 1.64 g of $N^\alpha$-(t-butyloxycarbonyl-alanyl-D-isoglutaminyl)-$N^\epsilon$-acetyl-lysine; melting point: 154°–155° C. (decomp.); $[\alpha]_D^{25} -13.1°$ (c 0.5, methanol).

Elementary Analysis for $C_{21}H_{37}N_5O_8 \cdot 1\ 1/5H_2O$: Calcd. (%): C 49.53, H 7.79, N 13.75, Found (%): C 49.44, H 7.49, N 13.73.

(3) In 50 ml of tetrahydrofuran were dissolved 1.41 g of 1-$\alpha$-O-benzyl-4,6-O-benzylidene-N-acetylmuramic acid and 0.38 g of N-hydroxysuccinimide, and 0.68 g of dicyclohexylcarbodiimide was added thereto with stirring under ice-cooling. After 30 minutes, the mixture was allowed to warm to room temperature, followed by allowing the mixture to react for 5 hours while stirring. The precipitated dicyclohexylurea was removed by filtration. The filtrate was concentrated, and the residue was dissolved in 5 ml of N,N-dimethylformamide to prepare an N,N-dimethylformamide solution of an N-hydroxysuccinimide ester of 1-α-O-benzyl-4,6-O-benzylidene-N-acetylmuramic acid.

Separately, 1.60 g of the $N^\alpha$-(t-butyloxycarbonyl-alanyl-D-isoglutaminyl)-$N^\epsilon$-acetyl-lysine obtained in (2) above was suspended in 3 ml of dichloromethane, and 3 ml of trifluoroacetic acid was added to the suspension with stirring under ice-cooling. After 5 minutes, the temperature was restored to room temperature, and the mixture was allowed to react for 1 hour. The reaction mixture was concentrated under reduced pressure, and to the residue was added 30 ml of a diethyl ether solution containing 0.66 ml of a 5N hydrochloric acid-dioxane solution under ice-cooling. The precipitated powder was collected by filtration and dissolved in 20 ml of N,N-dimethylformamide. To the resulting solution was added 0.33 ml of N-methylmorpholine with stirring under ice-cooling. To the solution were then added the above-described N,N-dimethylformamide solution of an N-hydroxysuccinimide ester of 1-α-O-benzyl-4,6-O-benzylidene-N-acetylmuramic acid and 0.33 ml of N-methylmorpholine. After 30 minutes, the mixture was allowed to warm to room temperature, and the reaction was conducted overnight. The reaction mixture was concentrated, and water was added to the residue. The precipitated powder was collected by filtration, washed successively with a 5% aqueous solution of citric acid and water and recrystallized from N,N-dimethylformamide-diethyl ether to obtain 2.08 g of $N^\alpha$-(1-α-O-benzyl-4,6-O-benzylidene-N-acetylmuramyl-alanyl-D-isoglutaminyl)-$N^\epsilon$-acetyl-lysine; melting point: 235°–236° C. (decomp.); $[\alpha]_D^{25}$ +59.7° (c 0.2, N,N-dimethylformamide).

Elementary Analysis for $C_{41}H_{56}N_6O_{13}.1\frac{3}{4}H_2O$: Calcd. (%): C 56.44, H 6.87, N 9.63, Found (%): C 56.47, H 6.66, N 9.33.

(4) In 40 ml of acetic acid was dissolved 1.50 g of the compound prepared in (3) above, and the solution was hydrogenolyzed in the presence of palladium-on-carbon in a hydrogen stream at room tempertature. The catalyst was removed by filtration, and the filtrate was concentrated. Diethyl ether was added to the residue, and the precipitated powder was collected by filtration. The powder was purified by silica gel chromatography using chloroform-methanol-acetic acid (4:1:0.1) as an eluent. The effluent was concentrated. A solution of the residue in 20 ml of water was passed through a column packed with a strongly acidic ion exchange resin ($H^+$ type), and the effluent was lyophilized to obtain 0.96 g of $N^\alpha$-(N-acetylmuramyl-alanyl-D-isoglutaminyl)-$N^\epsilon$-acetyl-lysine; melting point: 140°–142° C. (decomp.); $[\alpha]_D^{25}$ +11.6° (c 0.2, water, after 1 day).

Elementary Analysis for $C_{27}H_{46}N_6O_{13}.1\frac{1}{2}H_2O$: Calcd. (%): C 47.02, H 7.16, N 12.18, Found (%): C 46.86, H 6.98, N 12.14.

(5) In 1 ml of N,N-dimethylformamide were dissolved 0.20 g of the compound prepared in (4) above and 34 mg of 3-hydroxypyridine, and 75 mg of dicyclohexylcarbodiimide was added thereto with stirring under ice-cooling. After 30 minutes, the mixture was allowed to warm to room temperature, followed by reacting overnight. The precipitated N,N-dicyclohexylurea was removed by filtration, and the filtrate was concentrated. Diethyl ether was added to the residue, and the resulting powder was recrystallized from N,N-dimethylformamide-diethyl ether to obtain 0.16 g of $N^\alpha$-(N-acetylmuramyl-alanyl-D-isoglutaminyl)-$N^\epsilon$-acetyl-lysine 3-pyridyl ester.

Melting Point: 149°–152° C. (decomp.)
IR (KBr): 3290, 2940, 1760, 1640, 1545 $cm^{-1}$,
$[\alpha]_D^{25}$ +34.5° (c 0.4, N,N-dimethylformamide).
Elementary Analysis for $C_{32}H_{49}N_7O_{13}.2\frac{1}{4}H_2O$: Calcd. (%): C 49.26, H 6.91, N 12.56, Found (%): C 49.50, H 6.67, N 12.30.

EXAMPLE 2

(1) In the same manner as described in Example 1-(2), 1.50 g of $N^\alpha$-(t-butyloxycarbonyl-alanyl-D-isoglutaminyl)-lysine and 1.01 g of an N-hydroxy-5-norbornene-2,3-dicarboxyimide active ester of butyric acid were reacted to obtain 1.57 g of $N^\alpha$-(t-butyloxycarbonyl-alanyl-D-isoglutaminyl)-$N^\epsilon$-butyryl-lysine; melting point: 84°–87° C. (decomp.); $[\alpha]_D^{25}$ −12.2° (c 0.9, methanol).

Elementary Analysis for $C_{23}H_{41}N_5O_8.\frac{1}{2}H_2O$: Calcd. (%): C 52.66, H 8.07, N 13.35, Found (%): C 52.90, H 8.11, N 13.09.

(2) In the same manner as described in Example 1-(3), 1.50 g of the compound prepared in (1) above was reacted to obtain 2.25 g of $N^\alpha$-(1-α-O-benzyl-4,6-O-benzylidene-N-acetylmuramyl-alanyl-D-isoglutaminyl)-$N^\epsilon$-butyryl-lysine; melting point: 227°–228° C. (decomp.); $[\alpha]_D^{25}$ +56.3° (c 0.2, N,N-dimethylformamide).

Elementary Analysis for $C_{43}H_{60}N_6O_{13}.H_2O$: Calcd. (%): C 58.22, H 7.04, N 9.47, Found (%): C 57.98, H 6.89, N 9.43.

(3) In the same manner as described in Example 1-(4), 2.10 g of the compound prepared in (2) above was reacted to obtain 1.26 g of $N^\alpha$-(N-acetylmuramyl-alanyl-D-isoglutaminyl)-$N^\epsilon$-butyryl-lysine; melting point: 142° to 144° C. (decomp.); $[\alpha]_D^{25}$ 15.8° (c 0.7, water, after 2 days).

Elementary Analysis for $C_{29}H_{50}N_6O_{13}1\frac{1}{2}H_2O$: Calcd. (%): C 48.53, H 7.44, N 11.71, Found (%): C 48.81, H 7.17, N 11.81.

(4) In the same manner as described in Example 1-(5), 0.20 g of the compound prepared in (3) above was reacted to obtain 0.17 g of $N^\alpha$-(N-acetylmuramyl-alanyl-D-isoglutaminyl)-$N^\epsilon$-butyryl-lysine 3-pyridyl ester.

Melting Point: 117°–120° C. (decomp.).
$[\alpha]_D^{25}$ +38.5° (c 0.4, N,N-dimethylformamide).
IR (KBr): 3300, 2945, 1760, 1650, 1540 $cm^{-1}$.
Elementary Analysis for $C_{34}H_{53}N_7O_{13}.3H_2O$: Calcd. (%): C 49.69, H 7.24, N 11.93, Found (%): C 49.68, H 7.20, N 11.98.

EXAMPLE 3

(1) In the same manner as described in Example 1-(2), 1.10 g of $N^\alpha$-(t-butyloxycarbonyl-alanyl-D-isoglutaminyl))lysine and 0.69 g of an N-hydroxy-5-norbornene-2,3-dicarboxyimide active ester of hexanoic acid were reacted to obtain 1.17 g of $N^\alpha$-(t-butyloxycarbonyl-alanyl-D-isoglutaminyl)-$N^\epsilon$-hexanoyl-lysine; melting point: 116° to 118° C. (decomp.); $[\alpha]_D^{25}$ −12.1° (c 1.1, methanol).

Elementary Analysis for $C_{25}H_{45}N_5O_8.\frac{1}{2}H_2O$: Calcd. (%): C 54.33, H 8.39, N 12.67, Found (%): C 54.51, H 8.26, N 12.82.

(2) In the same manner as described in Example 1-(3), 1.00 g of the compound prepared in (1) above was reacted to obtain 1.53 g of $N^\alpha$-(1-α-O-benzyl-4,6-O-benzylidene-N-acetylmuramyl-alanyl-D-isoglutaminyl)-

N$^\epsilon$-hexanoyl-lysine; melting point: 221°–222° C. (decomp.); $[\alpha]_D^{25}$+56.1° (c 0.2, N,N-dimethylformamide).

Elementary Analysis for $C_{45}H_{64}N_6O_{13}.1\frac{1}{2}H_2O$: Calcd. (%): C 58.49, H 7.30, N 9.09, Found (%): C 58.47, H 7.12, N 9.05.

(3) In the same manner as described in Example 1-(4), 1.30 g of the compound prepared in (2) above was reacted to obtain 0.56 g of N$^\alpha$-(N-acetylmuramyl-alanyl-D-isoglutaminyl)-N$^\epsilon$-hexanoyl-lysine; melting point: 144° to 146° C. (decomp.); $[\alpha]_D^{25}$+14.6° (c 0.7, water, after 2 days).

Elementary Analysis for $C_{31}H_{54}N_6O_{13}.H_2O$: Calcd. (%): C 50.53, H 7.66, N 11.41, Found (%): C 50.61, H 7.49, N 11.19.

(4) In the same manner as described in Example 1-(5), 0.15 g of the compound prepared in (3) above was reacted to obtain 0.12 g of N$^\alpha$-(N-acetylmuramyl-alanyl-D-isoglutaminyl)-N$^\epsilon$-hexanoyl-lysine 3-pyridyl ester.

Melting Point: 146°–148° C. (decomp.).

$[\alpha]_D^{25}$+33.7° (c 0.4, N,N-dimethylformamide).

IR (KBr): 3295, 2925, 1760, 1640, 1540 cm$^{-1}$.

Elementary Analysis for $C_{36}H_{57}N_7O_{13}.2H_2O$: Calcd. (%): C 51.97, H 7.39, N 11.78. Found (%): C 52.22, H 7.13, N 11.80.

EXAMPLE 4

In the same manner as described in Example 1-(5), 0.15 g of N$^\alpha$-(N-acetylmuramyl-alanyl-D-isoglutaminyl)-N$^\epsilon$-octanoyl-lysine was reacted to obtain 0.13 g of N$^\alpha$-(N-acetylmuramyl-alanyl-D-isoglutaminyl)-N$^\epsilon$-octanoyl-lysine 3-pyridyl ester.

Melting Point: 115°–118° C. (decomp.).

$[\alpha]_D^{25}$+37.6° (c 0.4, N,N-dimethylformamide).

IR (KBRr): 3300, 2925, 1760, 1640, 1540 cm$^{-1}$.

Elementary Analysis for $C_{38}H_{61}N_7O_{13}.2H_2O$: Calcd. (%): C 53.07, H 7.61, N 11.40, Found (%): C 52.86, H 7.47, N 11.56.

EXAMPLE 5

In the same manner as described in Example 1-(5), 50 mg of N$^\alpha$-(N-acetylmuramyl-alanyl-D-isoglutaminyl)-N$^\epsilon$-butyryl-lysine and 8.9 mg of 2-mercaptopyridine were reacted to obtain 45 mg of N$^\alpha$-(N-acetylmuramyl-alanyl-D-isoglutaminyl)-N$^\epsilon$butyryl-lysine 2-pyridyl-thiol ester.

Melting Point: 142°–144° C. (decomp.).

$[\alpha]_D^{25}$+39.0° (c 0.4, N,N-dimethylformamide).

IR (KBr): 3350, 2925, 1820, 1650, 1540 cm$^{-1}$.

Elementary Analysis for $C_{34}H_{53}N_7O_{12}S.1\frac{1}{2}H_2O$: Calcd. (%): C 50.35, H 6.96, N 12.09, Found (%): C 50.52, H 7.16, N 11.92.

EXAMPLE 6

(1) In the same manner as described in Example 1-(2), 0.15 g of N$^\alpha$-(N-acetylmuramyl-valyl-D-isoglutaminyl)lysine and 63 mg of an N-hydroxy-5-norbornene-2,3-dicarboxyimide active ester of acetic acid were reacted to obtain 0.13 g of N$^\alpha$-(N-acetylmuramyl-valyl-D-isoglutaminyl)-N$^\epsilon$-acetyl-lysine.

Melting Point: 135°–138° C. (decomp.)

$[\alpha]_D^{25}$+14.5° (c 0.5, water, after 1 day)

Elementary Analysis for $C_{29}H_{50}N_6O_{13}.2\frac{1}{2}H_2O$: Calcd. (%): C 47.34, H 7.53, N 11.42, Found (%): C 47.53, H 7.33, N 11.46.

(2) In the same manner as described in Example 1-(5), 73 mg of the compound prepared in (1) above was reacted to obtain 66 mg of N$^\alpha$-(N-acetylmuramyl-valyl-D-isoglutaminyl)-N$^\epsilon$-acetyl-lysine 3-pyridyl ester.

$[\alpha]_D^{25}$+34.5° (c 0.4, N,N-dimethylformamide).

IR (KBr): 3295, 2930, 1760, 1650, 1540 cm$^{-1}$.

Elementary Analysis for $C_{34}H_{53}N_7O_{13}.2\frac{1}{2}H_2O$: Calcd. (%): C 50.24, H 7.19, N 12.06, Found (%): C 50.24, H 7.16, N 12.12.

EXAMPLE 7

(1) In the same manner as described in Example 1-(2), 0.90 g of N$^\alpha$-(N-acetylmuramyl-N-methylalanyl-D-isoglutaminyl)-lysine and 0.42 g of an N-hydroxy-5-norbornene-2,3-dicarboxyimide active ester of butyric acid were reacted to obtain 0.75 of N$^\alpha$-(N-acetylmuramyl-N-methyl alanyl-D-isoglutaminyl)-N$^\epsilon$-butyryl-lysine; melting point: 111°–11° C. (decomp.); $[\alpha]_D^{25}$+4.3° (c 0.5, water, after 1 day).

Elementary Analysis for $C_{30}H_{52}N_6O_{13}.H_2O$: Calcd. (%): C 49.85, H 7.53, N 11.63, Found (%): C 49.78, H 7.48, N 11.84.

(2) In the same manner as described in Example 1-(5), 0.40 g of the compound prepared in (1) above was reacted to obtain 0.36 g of N$^\alpha$-(N-acetylmuramyl-N-methylalanyl-D-isoglutaminyl)-N$^\epsilon$-butyryl-lysine 3-pyridyl ester.

$[\alpha]_D^{25}$+10.5° (c 0.4, N,N-dimethylformamide).

IR (KBr): 3300, 2925, 1760, 1650, 1540 cm$^{-1}$.

Elementary Analysis for $C_{35}H_{55}N_7O_{13}.1\frac{1}{2}H_2O$: Calcd. (%): C 51.98, H 7.18, N 12.13, Found (%): C 51.94, H 7.18, N 12.00.

EXAMPLE 8

(1) In 40 ml of N,N-dimethylformamide was dissolved 6.65 g of N$^\alpha$-(1-$\alpha$-O-benzyl-N-acetylmuramyl-alanyl-D-isoglutaminyl)-N$^\epsilon$-benzyloxycarbonyl-lysine benzyl ester. To the resulting solution were added 0.63 g of butyric acid, 0.87 g of N,N-dimethylaminopyridine, 0.96 g of 1-hydroxybenzotriazole and 1.47 g of dicyclohexylcarbodiimide with stirring under ice-cooling. After 30 minutes, the mixture was allowed to warm to room temperature, followed by reacting overnight with stirring. The precipitated dicyclohexylurea was removed by filtration, and the filtrate was concentrated under reduced pressure. Water was added to the residue, and the precipitated powder was collected by filtration, washed successively with a 5% citric acid aqueous solution, water, a 5% sodium hydrogen carbonate aqueous solution and water, and subjected to silica gel chromatography. The column was eluted with chloroform-methanol (9:1), and the effluent was concentrated. Recrystallization of the concentrate from chloroform-methanol-diethyl ether gave 3.26 g of N$^\alpha$-(1-$\alpha$-O-benzyl-6-O-butyryl-N-acetylmuramyl-alanyl-D-isoglutaminyl)-N$^\epsilon$-benzyloxycarbonyl-lysine benzyl ester; melting point: 216°–218° C. (decomp.); $[\alpha]_D^{25}$+53.5° (c 0.4, methanol).

Elementary Analysis for $C_{51}H_{68}N_6O_{15}.\frac{1}{2}H_2O$: Calcd. (%): C 60.40, H 6.86, N 8.29, Found (%): C 60.57, H 6.75, N 8.39.

(2) In 200 ml of acetic acid was dissolved 5.28 g of the compound prepared in (1) above, and the solution was hydrogenolyzed in the presence of palladium-on carbon in a hydrogen stream at room temperature. The catalyst was removed by filtration, and the filtrate was concentrated. The residue was subjected to gel-filtration chromatography using Sephadex LH-20 and eluted with a 0.2M acetic acid aqueous solution. The effluent was lyophilized to obtain 2.95 g of N$^\alpha$-(6-O-butyryl-N-acetylmuramyl-alanyl-D-isoglutaminyl)-lysine; melting point: 126°–128° C. (decomp.); $[\alpha]_D^{25} +24.6°$ (c 0.4, water, after 1 day).

Elementary Analysis for $C_{29}H_{50}N_6O_{13} \cdot 2H_2O$: Calcd. (%): C 47.93, H 7.49, N 11.56, Found (%): C 47.99, H 7.40, N 11.29.

(3) In 10 ml of N,N-dimethylformamide was dissolved 1.00 g of the compound prepared in (2) above, and 0.36 g of an N-hydroxy-5-norbornene-2,3-dicarboxyimide ester of formic acid and 0.32 ml of N-methylmorpholine were added thereto with stirring under ice-cooling. After 30 minutes, the mixture was allowed to warm to room temperature, followed by stirring overnight. The reaction mixture was concentrated, and the residue was subjected to silica gel chromatography using chloroform-methanol (7:3) as an eluent. The effluent was concentrated, and diethyl ether was added to the residue. The precipitated powder was collected by filtration. The powder was dissolved in water, and the solution was passed through a column packed with a strongly acidic ion exchange resin (H+ type). The effluent was lyophilized to obtain 0.66 g of $N^\alpha$-(6-O-butyryl-N-acetylmuramyl-alanyl-D-isoglutaminyl)-$N^\epsilon$-formyl-lysine; melting point: 123°–126° C. (decomp.); $[\alpha]_D^{25} +18.8°$ (c 0.4, methanol).

Elementary Analysis for $C_{30}H_{50}N_6O_{14} \cdot \frac{3}{4}H_2O$: Calcd. (%): C 49.21, H 7.09, N 11.48, Found (%): C 49.12, H 7.05, N 11.55.

(4) In the same manner as described in Example 1-(5), 0.40 g of the compound prepared in (3) above was reacted to obtain 0.41 g of $N^\alpha$-(6-O-butyryl-N-acetylmuramylalanyl-D-isoglutaminyl)-$N^\epsilon$-formyl-lysine 3-pyridyl ester.

$[\alpha]_D^{25} +27.8°$ (c 0.5, N,N-dimethylformamide).

IR (KBr): 3300, 2925, 1760, 1730, 1660, 1540 cm$^{-1}$.

Elementary Analysis for $C_{35}H_{53}N_7O_{14} \cdot 2H_2O$: Calcd. (%): C 50.53, H 6.91, N 11.79, Found (%): C 50.79, H 6.95, N 11.92.

EXAMPLE 9

(1) In the same manner as described in Example 8-(3), 0.90 g of $N^\alpha$-(6-O-butyryl-N-acetylmuramyl-alanyl-D-isoglutaminyl)-lysine and 0.39 g of an N-hydroxy-5-norbornene-2,3-dicarboxyimide active ester of butyric acid were reacted to obtain 0.90 g of $N^\alpha$-(6-O-butyryl-N-acetylmuramyl-alanyl-D-isoglutaminyl)-$N^\epsilon$-butyryl-lysine; melting point: 83°–86° C.; $[\alpha]_D^{25} +18.5°$ (c 0.6, water, after 1 day).

Elementary Analysis for $C_{33}H_{56}N_6O_{14} \cdot 1/2H_2O$: Calcd. (%): C 51.49, H 7.47, N 10.92, Found (%): C 51.38, H 7.19, N 10.83.

(2) In the same manner as described in Example 1-(5), 0.40 g of the compound prepared in (1) above was reacted to obtain 0.40 g of $N^\alpha$-(6-O-butyryl-N-acetylmuramylalanyl-D-isoglutaminyl)-$N^\epsilon$-butyryl-lysine 3-pyridyl ester.

$[\alpha]_D^{25} +24.6°$ (c 0.5, N,N-dimethylformamide).

IR (KBr): 3300, 2925, 1760, 1730, 1660, 1540 cm$^{-1}$.

Elementary Analysis for $C_{38}H_{59}N_7O_{14} \cdot 2H_2O$: Calcd. (%): C 52.22, H 7.27, N 11.22, Found (%): C 52.10, H 7.04, N 11.05.

The biological activities of the compounds (I) according to the present invention will be demonstrated by the following Test Examples 1 to 3. The compounds of the invention used in these test examples are as follows:

Compound No. 1

$N^\alpha$-(N-Acetylmuramyl-alanyl-D-isoglutaminyl)-$N^\epsilon$-acetyl-lysine 3-pyridyl ester

Compound No. 2

$N^\alpha$-(N-Acetylmuramyl-alanyl-D-isoglutaminyl)-$N^\epsilon$-butyryl-lysine 3-pyridyl ester

Compound No. 3

$N^\alpha$-(N-Acetylmuramyl-alanyl-D-isoglutaminyl)-$N^\epsilon$-hexanoyl-lysine 3-pyridyl ester

Compound No. 4

$N^\alpha$-(N-Acetylmuramyl-valyl-D-isoglutaminyl)-$N^\epsilon$-acetyl-lysine 3-pyridyl ester

Compound No. 5

$N^\alpha$(N-Acetylmuramyl-N-methylalanyl-D-isoglutaminyl)-$N^\epsilon$-butyryl-lysine 3-pyridyl ester

Compound No. 6

$N^\alpha$-(6-O-Butyryl-N-acetylmuramyl-alanyl-D-isoglutaminyl)-$N^\epsilon$-formyl-lysine 3-pyridyl ester

Compound No. 7

$N^\alpha$-(6-0-butyryl-N-acetylmuramyl-alanyl-D-isoglutaminyl)-$N^\epsilon$-butyryl-lysine 3-pyridyl ester

TEST EXAMPLE 1

Shared Antigenic Determinant between Compound of this Invention and BCG, and Potent Immunogenic Activity of Compound of this Invention as Hapten

I. Preparation of MDP-Related Hapten-Modified Autologous Cells

One to five millimols of Compound No. 1 and syngeneic mouse spleen cells (10$^8$) from which erythrocytes had been removed were incubated at 37° C. for 20 minutes with shaking. The cells were then washed with 5% fetal bovine serum-containing culture media, RPMI 1640, to prepare $N^\alpha$-(N-acetylmuramyl-alanyl-D-isoglutaminyl)-$N^\epsilon$-acetyl-lysine-modified syngeneic spleen cells (hereinafter referred to as "MDP-Lys(L2)-modified syngeneic spleen cells"), i.e., MDP-related hapten-modified autologous cells.

In accordance with the same procedures as described above, the following syngeneic spleen cells modified with Compound No. 2, 3, 4, 5, 6 or 7 were prepared:

With Compound No. 2: MDP-Lys(L4)-modified syngeneic spleen cells

With Compound No. 3: MDP-Lys(L6)-modified syngeneic spleen cells

With Compound No. 4: MDP(V)-Lys(L2)-modified syngeneic spleen cells

With Compound No. 5: MDP(MeAla)-Lys(L4)-modified syngeneic spleen cells

With Compound No. 6: L4-MDP-Lys(L1)-modified syngeneic spleen cells

With Compound No. 7: L4-MDP-Lys(L4)-modified syngeneic spleen cells

The above obtained MDP-related hapten-modified autologous cells were used as stimulating cells.

II. Preparation of Responding Cells

Responding Cells (1) and (2) that reflect reactivity of test animals were prepared as follows:

C3H/HeN mice were primed to BCG by inoculating s.c. 1 mg of BCG at three week interval after exposure of X-irradiation to whole body at a dose of 150 R, and the spleen cells were prepared from the immunized mouse. The resulting spleen cells are designated as Responding Cells (1). On the other hand, spleen cells were prepared from a non-immunized C3H/HeN mouse and are designated as Responding Cells (2).

III. Test for Confirmation of Shared Antigenic Determinant and Potent Immunogenic Activity as Hapten Responding Cells (1) or (2) ($4 \times 10^5$/well) were cultured with each of the above-prepared stimulating cells ($4 \times 10^5$/well) in a Falcon microculture plate (3072) at 37° C. for 5 days. On the fourth day, 0.5 to 1 $\mu$Ci/well of tritiated thymidine was added to the culture. On the fifth day, the cells were harvested, and the amount of tritiated thymidine incorporated in the cells was determine. An increase of this amount in the case of using Responding Cells (1) as compared with the case of using Responding Cells (2) indicates that the proliferative response of T cells was induced, i.e., the tested compound has shared antigenic determinant to BCG and suitability as a hapten. The results obtained are shown in Table 1 below.

TABLE 1

T Cell Proliferative Response Induced by MDP-Related Hapten-Modified Syngeneic Spleen Cells Immunization

| Stimulating Cells | Increase of Tritiated Thymidine Incorporation [(1)/(2)] |
| --- | --- |
| MDP-Lys(L2)-Modified Syngeneic Spleen Cells | 9.5 |
| MDP-Lys(L4)-Modified Syngeneic Spleen Cells | 4.2 |
| MDP-Lys(L6)-Modified Syngeneic Spleen Cells | 1.2 |
| MDP(V)-Lys(L2)-Modified Syngeneic Spleen Cells | 3.1 |
| MDP(MeAla)-Lys(L4)-Modified Syngeneic Spleen Cells | 4.7 |
| L4-MDP-Lys(L1)-Modified Syngeneic Spleen Cells | 6.0 |
| L4-MDP-Lys(L4)-Modified Syngeneic Spleen Cells | 2.1 |

TEST EXAMPLE 2

Study on whether Helper T Cells Reactive to Compounds of this Invention are Present in Spleen Cells from BCG-Immunized Mice I. Preparation of Test Model (A) Preparation of Helper T Cell Source A C3H/HeN mouse was twice immunized by subcutaneously injecting 1 mg of BCG at three week intervals. The spleen cells from the immunized mouse were irradiated with 850 R X-rays to obtain a helper T cell source ($3.0 \times 10^6$/well). Spleen cells of a non-immunized C3H/HeN mouse were irradiated with X-rays in the same manner to prepare a control ($3.0 \times 10^6$/well).

(B) Preparation of Responding Cells ($T_E$ Cell Source):

Spleen cells ($1.5 \times 10^6$/well) taken from a C3H/HeN mouse were used.

(C) Preparation of Stimulating Cells

Syngeneic spleen cells ($2 \times 10^5$/well) modified with 0.5 mM of trinitrobenzene sulfonate, which is a model of a tumor associated antigen (i.e., a hapten other than the MDP-related compounds); syngeneic spleen cells ($2 \times 10^6$/well) modified with 1 mM of MDP-Lys(L2); and a mixture of both were prepared.

II. Test for Confirmation of Helper T Cell Induction

The aforesaid helper T cell source, responding cells and stimulating cells were mixed and incubated at 37° C. for 5 days. After the incubation, the incubated cells were mixed with X-5563 syngeneic tumor cells, to which TNP had been conjugated and which had further been labeled with $^{51}$Cr, as target cells. Cell lysis of the X-5563 syngeneic tumor cells was observed by a $^{51}$Cr release assay and expressed in terms of cytotoxicity, In this test, the higher the cytotoxicity, the higher the induction of $T_E$ cells. The above fact means that helper T cells which can be activated by the compounds of this invention exist in the spleen cells of BCG-immunized mice. The test results shown in Table 2 below prove the existence of helper T cells which is reactive with the compounds of this invention in the spleen cells of the BCG-immunized mouse.

TABLE 2

Helper T Cell Activity Specific to Compound of this Invention in Spleen Cells from BCG-Immunized Mice

| Helper T Cell Source | Cytotoxicity (%) $T_E$ Cell:Target Cell Ratio | | |
| --- | --- | --- | --- |
| | 5:1 | 10:1 | 20:1 |
| Spleen cells of BCG-immunized mouse | 17.3 | 26.0 | 33.0 |
| Control | 4.0 | 3.0 | 0 |

The above results of Table 2 are obtained in case of using a mixture of the TNP-modified syngeneic spleen cells and the MDP-Lys(L2)-modified syngeneic spleen cells as stimulating cells. When tests were conducted under the same conditions but using each of them individually, no significant production of cytotoxicity was observed.

TEST EXAMPLE 3

Effect of Compound of this Invention on Enhancement of Antitumor Immunity

I. Test Animal

C3H/HeN mice

II. Preparation of Tumor Specific $T_E$ Cells in vivo

MDP-Lys(L2)-modified syngeneic X5563 tumor cells (traced with mitomycin) were prepared by using Compound No. 1 according to the methiod of Fujiwara et al. (J. Immunol., 124, 863-869 (1980)).

For the purpose of inducing helper T cells reactive to the MDP-related hapten in mouse spleen cells, a mouse having been irradiated with 150 R X-rays was twice immunized by subcutaneously injecting 1 mg of BCG. The immunized mouse further received 5 intraperitoneal injections of the aforesaid MDP-Lys(L2)-modified syngeneic X5563 tumor cells ($1 \times 10^7$) treated with mitomycin. The immunization with the MDP-Lys(L2)-modified syngeneic tumor cells aimed at enhanced generation of $T_E$ cells reactive to a tumor associated antigen in the mouse spleen cells. Spleen cells ($2 \times 10^7$) were prepared from the treated mouse and used as a treated group. As controls, spleen cells from a mouse which had been treated only with 5 intraperitoneal injections of the MDP-Lys(L2)-modified syngeneic X5563 tumor cells treated with mitomycin (Control Group 1) and spleen cells from a mouse which had received no treatment at all (Control Group 2) were prepared.

II. Test for Enhancement of Antitumor Immunity $T_E$ cells prepared above and viable X5563 tumor cells ($1 \times 10^5$) were mixed and subcutaneously inoculated to an untreated mouse. The tumor diameter was measured with the passage of time to determine the tumor growth. The same procedures were carried out on the control groups. The results as shown in Table 3 below demonstrate a remarkable inhibitory effect on tumor growth in the treated group, i.e., an activity of the compound of this invention to potentiate antitumor immunity.

The same procedures as described above were repeated using L4-MDP-Lys(L1)-modified syngeneic antitumor cells prepared with Compound No. 6 of the present invention. The results obtained are shown in Table 4 below.

The antitumor activity observed in the above tests is specific to S5563 tumor cells but is not observed on the other tumor cells, e.g., syngeneic hepatoma MH134 cells.

It was proved by this test example that proper immunization procedures using the compound of this invention induce helper T cells, which, in turn, induce tumor specific $T_E$ cells thereby enhancing antitumor immunity.

TABLE 3

Inhibitory Effect on Tumor Growth
(MDP-Lys(L2)-Modified Syngeneic Tumor Cells)

| Test Group | Tumor Diameter (mm) | |
| --- | --- | --- |
| | 9th Day | 12th Day |
| Treated Group | <3 | <3 |
| Control Group 1 | 7.5 | 13.0 |
| Control Group 2 | 8.8 | 14.0 |

TABLE 4

Inhibitory Effect on Tumor Growth
(L4-MDP-Lys(L1)-Modified Syngeneic Tumor Cells)

| Test Group | Tumor Diameter (mm) | |
| --- | --- | --- |
| | 9th Day | 12th Day |
| Treated Group | <3 | <3 |
| Control Group 1 | 5.7 | 11.3 |
| Control Group 2 | 8.8 | 14.0 |

TEST EXAMPLE 5

Suppression of Tumor Growth in Tumor-Bearing Mice Obtained by Augmented Induction of Tumor Specific Immunity Ten female C3H/HeN mice at 7 to 9 weeks of age was irradiated with 150 R X-ray and then immunized by subcutaneously injecting 1 mg and 0.5 mg of BCG at 4 week interval. After 3 weeks from the later immunizing, the mice received intradermal injection of X5563 tumor cells ($1 \times 10^6$/head). Seven days after the injection of tumor cells, 1 mM of Compound No. 4 in 200 μl of Angioconray (a product of Daiichi Seiyaku Co., Ltd.) was injected intratumorally to the mice. The tumor diameter was measured with the passage of time to determine the tumor growth. The same procedure was carried out on the control. The results obtained are shown in Table 5 below.

TABLE 5

| Mice Injected with Compound No. 4 Mouse No. | Tumor Diameter (mm) | | | |
| --- | --- | --- | --- | --- |
| | 0 | 5 | 7 | 9 (days) |
| 1 | 10.8 | 9.8 | 9.5 | 10.3 |
| 2 | 10.5 | 9.5 | 8.8 | 9.0 |
| 3 | 10.3 | 15.2 | 15.2 | 16.5 |
| 4 | 9.5 | 9.0 | 0 | 0 |
| 5 | 9.3 | 9.5 | 10.0 | 13.0 |
| 6 | 8.8 | 7.3 | 4.8 | 0 |
| 7 | 8.5 | 8.8 | 8.5 | 8.3 |
| 8 | 8.0 | 8.3 | 0 | 0 |
| 9 | 7.8 | 8.0 | 8.3 | 7.8 |
| 10 | 10.3 | 7.8 | 5.0 | 0 |
| Control | 7.5 | 13.8 | 17.0 | 18.5 |

As is apparent from Table 5, in 8 mice out of 10 mice tested, the inocurated tumor cells disappeared within 7 to 9 days or the tumor growth was inhibited. Therefore, it was proved by this test example that the compound of this invention had an excellent antitumor activity.

While the invention has been described in detail and with reference to specific embodiments thereof, it will be apparent to one skilled in the art that various changes and modification can be made therein without departing from the spirit and scope thereof.

What is claimed is:

1. A muramylpeptide derivative represented by the formula:

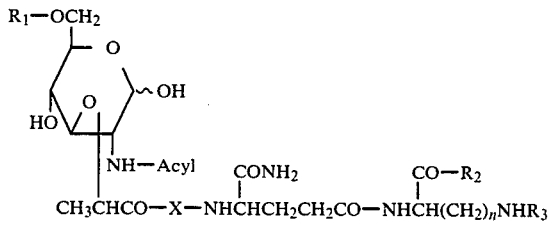

wherein $R_1$ represents a hydrogen atom or a fatty acid residue having from 2 to 10 carbon atoms; —$COR_2$ represents an active ester group; $R_3$ represents a fatty acid residue having from 1 to 10 carbon atoms; X represents an alanine, N-methylalanine or valine residue; "Acyl" represents a fatty acid residue having from 2 to 6 carbon atoms; and n represents an integer of from 1 to 6.

2. $N^\alpha$-(N-Acetylmuramyl-alanyl-D-isoglutaminyl)-$N^\epsilon$-acetyl-lysine 3-pyridyl ester.

3. $N^\alpha$-(N-Acetylmuramyl-alanyl-D-isoglutaminyl)-$N^\epsilon$-butyryl-lysine 3-pyridyl ester.

4. $N^\alpha$-(N-Acetylmuramyl-alanyl-D-isoglutaminyl)-$N^\epsilon$-hexanoyl-lysine 3-pyridyl ester.

5. $N^\alpha$-(N-Acetylmuramyl-alanyl-D-isoglutaminyl)-$N^\epsilon$-octanoyl-lysine 3-pyridyl ester.

6. $N^\alpha$-(N-Acetylmuramyl-alanyl-D-isoglutaminyl)-$N^\epsilon$-butyryl-lysine 2-pyridylthiol ester.

7. $N^\alpha$-(N-Acetylmuramyl-valyl-D-isoglutaminyl)-$N^\epsilon$-acetyl-lysine 3-pyridyl ester.

8. $N^\alpha$-(N-Acetylmuramyl-N-methylalanyl-D-isoglutaminyl)-$N^\epsilon$-butyryl-lysine 3-pyridyl ester.

9. $N^\alpha$-(6-O-Butyryl-N-acttylmuramyl-alanyl-D-isoglutaminyl)-$N^\epsilon$-formyl-lysine 3-pyridyl ester.

10. $N^\alpha$-(6O-Butyryl-N-acetylmuramyl-alanyl-D-isoglutaminyl)-$N^\epsilon$butyryl-lysine 3-pyridyl ester.

11. A muramylpeptide derivative as in claim 1, wherein $R_2$ is selected from the group consisting of a p-nitrophenoxy group, a 2,4-dinitrophenoxy group, a 2,4,5-trichlorophenoxy group, a pentachlorophenoxy group, a pentafluorophenoxy group, a phenylthio group, a succinimidooxy group, a benzotriazolyloxy group, a 5-norbornene-2,3-dicarboxyimidooxy group, a phthalimidooxy group, a morpholinooxy group, a piperidinooxy group, a 2-pyridylthio group, a 2-pyridyloxy group, a 3-pyridyloxy, an 8-quinolyloxy group and a 2-hydroxyphenoxy group.

* * * * *